(12) United States Patent
Assmus et al.

(10) Patent No.: US 8,778,617 B2
(45) Date of Patent: Jul. 15, 2014

(54) METHOD FOR DETERMINING THE BINDING CONSTANT OF HIGH AFFINITY COMPOUNDS

(75) Inventors: Frauke Assmus, Basel (CH); Holger Fischer, Grellingen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/578,848

(22) PCT Filed: Feb. 22, 2011

(86) PCT No.: PCT/EP2011/052550
§ 371 (c)(1),
(2), (4) Date: Aug. 14, 2012

(87) PCT Pub. No.: WO2011/104210
PCT Pub. Date: Sep. 1, 2011

(65) Prior Publication Data
US 2012/0309109 A1      Dec. 6, 2012

(30) Foreign Application Priority Data

Feb. 25, 2010   (EP) .................................... 10154696

(51) Int. Cl.
*G01N 33/53*    (2006.01)
*B01D 61/00*    (2006.01)
*B01D 53/22*    (2006.01)

(52) U.S. Cl.
USPC .......... 435/7.1; 210/634; 210/653; 210/257.2

(58) Field of Classification Search
CPC ...... G01N 33/558; B01D 61/00; B01D 61/24; B01D 53/22
See application file for complete search history.

(56) References Cited

U.S. PATENT DOCUMENTS

2003/0213740 A1   11/2003   Creasey
2007/0215538 A1    9/2007   Periana et al.

OTHER PUBLICATIONS

International Search Report for PCT/EP2011/052550 dated May 4, 2011.
Kurkov et al., AAPS Pharmscitech (XP002632913), 11(3):1152-1158 (Sep. 2010).
Kratochwil et al., Biochemical Pharmacology (XP008122771), 64(9):1355-1374 (Nov. 1, 2002).
Sparrow et al., Analytical Biochemistry (XP024826764), 123(2):255-264 (Jul. 1, 1982).

*Primary Examiner* — Shafiqul Haq

(57) ABSTRACT

The invention relates to a method for determining the binding constant of a compound of interest to proteins comprising the following steps: a) adding the high affinity compound to a two-chamber system, wherein the two chambers are separated by a semipermeable membrane, which is permeable for the compound of interest, and determining the amount of the high affinity compound of interest in one of the chambers after the distribution equilibrium has been reached, b) adding a sink compound to one of the chambers whereby the sink compound can not permeate the membrane, and determining the distribution coefficient of the compound of interest to the sink compound after the distribution equilibrium has been reached, c) adding an unspecific protein to the other chamber, whereby the unspecific protein can not permeate the membrane, and determining the distribution coefficient of the compound of interest to the unspecific protein in presence of a sink compound after the distribution equilibrium has been reached, and d) determining the binding constant of the test compound with the distribution coefficient of steps b) and c).

9 Claims, 12 Drawing Sheets

METHOD FOR DETERMINING THE BINDING CONSTANT OF HIGH AFFINITY COMPOUNDS

RELATED APPLICATIONS

This application is the National Stage of International Application No. PCT/EP2011/052550, filed Feb. 22, 2011, which claims the benefit of European Application No. 10154696.8, filed Feb. 25, 2010, which is hereby incorporated by reference in its entirety.

The success of a compound as drug is not only dependent of its potency, but rather of the optimal balance between the drug's strength, drug interaction, safety, pharmacokinetics, and productions costs.

Before the compound can be effective at the receptor its release, absorption, and distribution are of considerable influence. Only a free drug (not bound) can be effective on the receptor. If the drug binds too strong to proteins, the intensity of its pharmacological response can be reduced and it can have also an effect on the distribution volume, metabolization, and elimination of the drug.

Is it essential to maximize the generation of an in vitro data set through High Throughput-ADME Screens (A=absorption, D=distribution, M=metabolism, E=excretion) to get the chemists a feedback for finding a substance with the best physicochemical properties and to understand the relationship between chemical structure and physicochemical parameters.

A known method for determining the protein binding is e.g. an equilibrium dialysis. Start point of this method are two chambers, a sample chamber and a protein chamber, which are separated by a semipermeable membrane. The MWCO of the membrane is chosen such that the test substance is able to permeate but that the macromolecule (e.g protein) is retained. A known concentration and volume of the test substance is placed in the sample chamber. Then, a known concentration of the protein is placed in the protein chamber in a volume equivalent to that one of the substance in the sample chamber. As the test substance diffuses across the membrane some will bind to the protein and some will remain free in solution. The lower the affinity of the interaction, the higher the concentration of the test substance that will remain unbound at any time. The diffusion of the test substance across the membrane and binding of the test substance continues until equilibrium has been reached. At equilibrium, the concentration of the test compound free in solution is the same in both chambers. In the protein chamber, however, the overall concentration of the test substance is higher due to the bound test substance (if the test compounds binds to the protein). The concentration of free test substance in the sample chamber can then be used to determine the binding characteristics of the test compound.

Another method is the use of the BIAcore technology, whereby one of the binding partners is immobilized on a sensor chip. The other binding partner flows through the chip which is placed in a micro cell. The detection of the binding relies on the phenomenon of "surface plasmon resonance" (SPR), small changes in the reflection of monochromatic light from a metallic chip that occurs when the chip's surface binds a protein or other molecule.

However, all these methods are not suitable for determining the protein binding capability of high affinity substances in a High Throughput-Assay as it is not possible to differentiate between 99% and 99.99% binding with a high throughput of substances. The reason is that the concentration of the free test substance, which is what is analyzed in the end, is to low to be quantified.

With high affinity drugs, small changes in the amount of bound substances can have a profound influence on the free fraction in the body (see table below) and thereby influence on effect and side effects. Therefore, it is of high importance to make a measurement, in this very range.

Example with a difference of 4%:

| | | |
|---|---|---|
| 99% → 95% Binding | 1% free → 5% free | Factor 5 |
| 80% → 76% Binding | 20% free → 24% free | Factor 1.2 |

Therefore, the present invention provides a method for determining the binding constant of a high affinity compound of interest to proteins comprising the following steps:
a) adding the high affinity compound to a two-chamber system, wherein the two chambers are separated by a membrane which is permeable for the compound of interest, and determining the amount of the high affinity compound of interest in one of the chambers after the distribution equilibrium has been reached,
b) adding a sink compound to one of the chambers (sink chamber) whereby the sink compound can not permeate the membrane, and determining the distribution coefficient of the compound of interest to the sink compound after the distribution equilibrium has been reached,
c) adding an unspecific protein to the other chamber (protein chamber), whereby the unspecific protein can not permeate the membrane, and determining the distribution coefficient of the compound of interest to the unspecific protein in presence of a sink compound after the distribution equilibrium has been reached, and
d) determining the binding constant of the test compound with the distribution coefficient of steps b) and c).

The steps a), b), and steps c) can be performed consecutively, or they can be performed in parallel (see FIG. 3).

Therefore, the present invention also provides a method for determining the binding constant of a high affinity compound of interest to proteins comprising the following steps:
a) providing two-chamber systems for parallel performance wherein the two chambers of each system are separated by a membrane which is permeable for the compound of interest and adding the high affinity compound to a two-chamber system, and determining the amount of the high affinity compound of interest in one of the chambers after the distribution equilibrium has been reached,
b) adding the high affinity compound and a sink compound to one of the chambers of a second chamber system (sink chamber) whereby the sink compound can not permeate the membrane, and determining the distribution coefficient of the compound of interest to the sink compound after the distribution equilibrium has been reached,
c) adding the high affinity compound and a sink compound to one of the chambers of a third chamber system (sink chamber) and adding an unspecific protein to the other chamber (protein chamber), whereby the unspecific protein can not permeate the membrane, and the distribution coefficient of the compound of interest to the unspecific protein in presence of a sink compound after the distribution equilibrium has been reached, and
d) determining the binding constant of the test compound with the distribution coefficient of steps b) and c), wherein the steps a), b), and c) are performed in parallel.

Furthermore, the present application provides the use of a sink compound for determining the binding constant of a high affinity test compound.

A sink compound is a substance, which significantly lowers the affinity of high affinity test substances to an unspecific protein. Significantly lower the affinity means that the difference between the amount of bound test substance to the unspecific protein in the presence and absence of the sink compound is statistically relevant ($p<0.05$, preferably, $p<0.01$). To avoid that the sink compound crosses the membrane, but allowing the test compound to pass it, the size of the sink compound is preferably bigger by factor 2 than the size of the test compound. Preferably, a sink compound is a complexing agent. More preferably, the sink compound is Polyvinylpyrrolidone (PVP), most preferably, the sink compound is Polyvinylpyrrolidone K-25 (PVP 25, PVP K-25). For the purpose of the above mentioned method a combination of sink compounds can be used, e.g. PVP and Cyclodextrin.

The term "high affinity compound" as used herein, refers to a compound of which under physiological conditions and in the presence of a surplus of plasma protein (e.g. Albumin) at least 95% of the total amount is bound to said plasma protein (=at most 5% of the total amount of said compound are in free form). Preferably, at least 97% are bound, more preferably, at least 98% and most preferably, at least 99% are present in bound form. Physiological conditions are defined as pH 7.0 and 37° C. In terms of the present invention, a high affinity compound or test compound is preferably a drug.

The term "test substance" or "test compound" as used herein refers to a high affinity compound.

The term "binding constant" refers to constant that describes the binding affinity between two molecules at equilibrium. It describes the state of equilibrium between free and bound test substance.

The term "bound substance" or "bound compound" as used herein refers to a substance or compound which is bound to a protein, (in particular to an unspecific protein) or to the sink compound. The term "fractional occupation" refers to the fraction of test compounds that is bound. In other words, it is the proportion between the amount of test compound bound in equilibrium to a sink compound ($c_{bound\ test\ substance}$) and the total amount of test compound ($c_{total\ test\ substance}$).

$$\text{fractional occupation} = \text{fraction bound} = \frac{c_{bound\ test\ substance}}{c_{total\ test\ substance}}$$

An unspecific protein binds in contrast to a specific protein to a broad range of compounds (unselective binding). Unspecific proteins are in particular plasma proteins, such as e.g. serum albumin and $\alpha 1$ acid glycoprotein. Preferably, the unspecific protein is human serum albumin (HSA).

The membrane used in the method of the present invention is a semipermeable membrane. A semipermeable membrane is a membrane which allows a selected species of molecules to pass through it by diffusion. Semipermeable membranes for the above mentioned assay can be passed by the high affinity compound (and the buffer), but not by the sink compound or the unspecific protein. Preferably, the semipermeable membrane is a size selective membrane.

Semipermeable membranes can be characterized by Molecular Weight Cut Off (MWCO). Preferably, MWCO is approximately half of the molecular weight of the sink compound or the unspecific protein, whichever is the smaller. Also preferred is a proportion of 22 to 27 between the molecular weights of the test substance and the sink compound or the unspecific protein, whichever is the smaller. More preferably, the proportion is about 25. Suitable membranes for the methods of the present invention are commercially available, e.g. dialysis membranes.

Preferably, the concentration of unspecific protein used in the assay corresponds to the concentration of the protein in vivo. For HSA, the physiological concentration is around 60 mM.

The concentration of the sink compound for the optimal performance of the method of the invention can be determined with performing the method of the invention with different concentrations of the sink compound (i.e. serial dilution).

The assay is performed in a two chamber system, wherein the two chambers are separated by a semipermeable membrane. The permeability of the membrane is chosen such that the test substance can pass through the membrane, but not neither the sink compound nor the unspecific protein.

The measurements of the method of the invention (steps a), b), and steps c) and can be performed in parallel (see FIG. 3) or consecutively. Preferably, the measurements are made in parallel. In the following a preferred embodiment is described: For the reference experiment (step a) of the above described method), the compound of interest is added to one of the chambers (see FIG. 2 B) and the distribution of the compound is determined in this system after the distribution equilibrium has been reached whereby the mass of the compound in at least one of the chambers is determined after distribution equilibrium has been reached.

For binding experiment 1 (step b) of the above described method), the compound of interest and the sink compound are added to chamber in a different two chamber system than used for performing the reference experiment (see also FIG. 2 B). After the equilibrium of the binding system has been reached the amount of high affinity compound in the chamber without the sink compound (protein chamber) is measured and the distribution coefficient of the compound of interest to the sink compound is determined.

For binding experiment 2 (step d)) of the above described method), the compound of interest and the sink compound are added to a chamber (sink chamber) in a different two chamber system than used for performing the reference or binding experiment (see FIG. 2 C) and an unspecific protein is added to the chamber without sink compound (protein chamber). After an equilibrium has reached, the amount of free test substance (not bound to the sink compound) in the sink chamber is measured and the distribution coefficient of the compound of interest to the unspecific protein in the presence of the sink compound is determined.

The binding constant of the high affinity compound is determined as follows:

The binding of a test compound to an unspecific protein is a reversible process which can be described by the following equilibrium (Lindup, W. E., Plasma protein binding of drugs—some basic and clinical aspects, in Progress in Drug Metabolism, L. F. C. J. W. Bridges, G. G. Gibson, Editor. 1987. p. 141-185)

$$[T_u] + [P] \leftrightarrows [T \cdot P]$$

$$K_P = \frac{[T \cdot P]}{[T_u] * [P]}$$

[P]=concentrations of the unspecific protein
[$T_u$]=concentrations of test compound not bound to unspecific protein.

$K_P$=Binding constant of the test compound to the unspecific protein

[T·P]=concentration of test compound bound to nonspecific protein when equilibrium is reached The binding constant $K_P$ can be converted to the fraction unbound $f_u$ with the following formula derived from the law of mass:

$$f_u = 1 - f_b = \frac{100}{1 + K_P * [P]} \quad (1)$$

$f_b$=fraction of test compound bound to the unspecific protein

The binding constant to unspecific protein ($K_P$) (2) can be calculated from the combination of partition coefficients to sink compound ($DC_{sink}$) (3) and to the unspecific protein in the presence of the sink compound ($DC_{P'}$) (3).

$$K_P = DC_{sink} * DC_{P'} \quad (2)$$

From Binding Study I (with sink compound, FIG. 2B):

$$DC_{sink} = \frac{[T - \text{Sink}]}{[T_{u(sink)}]} = \frac{m_{Tb(sink)}}{m_{u(sink)}} * \frac{V_{total} - V_{sink}}{V_{sink}} = \frac{m_{T(ref)} - m_{Tu(sink)}}{m_{Tu(sink)}} \quad (3)$$

$m_{T(ref)}$=Mass of test compound in equilibrium, in the absence of the sink compound and the unspecific protein (measured in one of the chambers)

$m_{Tu(sink)}$=Mass of unbound test compound in equilibrium, in presence of the sink compound From Binding study II (system with sink compound and high affinity compound, FIG. 2C):

$$DC_{P'} = \frac{[T - P']}{[T_{u(sink)}]} = \frac{m_{Tb(P')}}{m_{Tu(P')}} * \frac{V_{total} - V_P}{V_P} = \frac{m_{T(ref)} - m_{Tu(P')}}{m_{Tu(P')}} \quad (4)$$

[T–P']=Concentration of bound test compound to unspecific protein in the presence of the sink compound

[T–Sink]=Concentration of test compound bound to the sink compound $m_{Tb(P')}$=Mass of test compound bound to the unspecific protein in equilibrium, in the system with the sink compound and the unspecific protein $m_{Tu(P')}$=Mass of test compound not bound to the unspecific protein in equilibrium in the system with the sink compound and the unspecific protein $V_{total}$ is total volume in the dialysis chamber (e.g. 200 µl)
$V_P$ is the volume of unspecific protein
$V_{sink}$ is the volume of the sink compound Volumes can be calculated from the density and the mass of the applied material V=mass/density (e.g. Density of human serum albumin: $\rho_{HSA}$=1.4 g/cm³, density of PVP25: $\rho_{PVP}$=1.2 g/cm³).

The amount of free and/or bound test substance can be determined spectrophotometrically directly in a spectrophotometer or after separation in a HPLC system.

For all reference and binding experiments, the chamber systems are preferably incubated under room temperature and normal pressure (e.g. overnight (about 12 hours)). For accelerating the achievement of the equilibrium the chamber can be shaken (preferably for about 1 to 3 hours, more preferably for 1 to 2 hours, most preferably for about 1 hour).

In a preferred embodiment, the method of the present invention is performed in parallel in a plate comprising a plurality of a two chamber system. These parallel performed assays be identical or they can differ e.g. in the identity or the concentration of the high affinity compound.

Having now generally described this invention, the same will become better understood by reference to the specific examples, which are included herein for purpose of illustration only and are not intended to be limiting unless otherwise specified, in connection with the following figures.

FIGURES

FIG. 1 shows a dialysis chamber system consisting of 10 Teflon™ bars wherein 8 of the Teflon™ bars have 12 drill holes on each site and two have 12 drill holes on one side (FIG. 1A). Said drill holes have the form of a half cylinder (see FIG. 1B) so that two bars together form a row of 12 cylindrical wells (rows A to I). Between the Teflon™ bars semipermeable membranes (M) are inserted such that each cylindrical well is divided into two half cylindrical chambers. The 10 Teflon™ bars with the membranes are assembled with two stainless steel connecting rods (R).

FIG. 2 shows the dialysis chamber system during an assay. The chamber comprises two chambers (chamber 1, chamber 2) which are separated by a membrane M. The size selective membrane M separates the two chambers and is permeable for the test compound but not for the sink compound or the unspecific protein. Test compound: ⊘; unspecific protein: △; the sink compound: ▨ . The encircled chamber number indicates the chamber from which a sample is taken for measurement. FIG. 2A) shows a schematic representation of the situation in the chamber system under reference conditions, whereby the test compound distributes evenly in the chamber system. FIG. 2B) shows a schematic representation of the situation in the chamber system with the test compound and the sink compound. Test compound and sink compound are added to chamber 1 and influences the distribution of the test compound as only unbound test compound can cross the membrane. FIG. 2C) shows a schematic representation of the situation in the chamber system with test compound, the sink compound, and the unspecific protein. Test compound and sink compound are added to chamber 1 and the unspecific protein is added to chamber 2. The sink compound reduces the amount of unbound test compound available for the unspecific protein. FIG. 2D) shows a schematic representation of the situation in the chamber system with a prior art assay. A high percentage of the test compound is bound to the unspecific protein.

Figure 5:
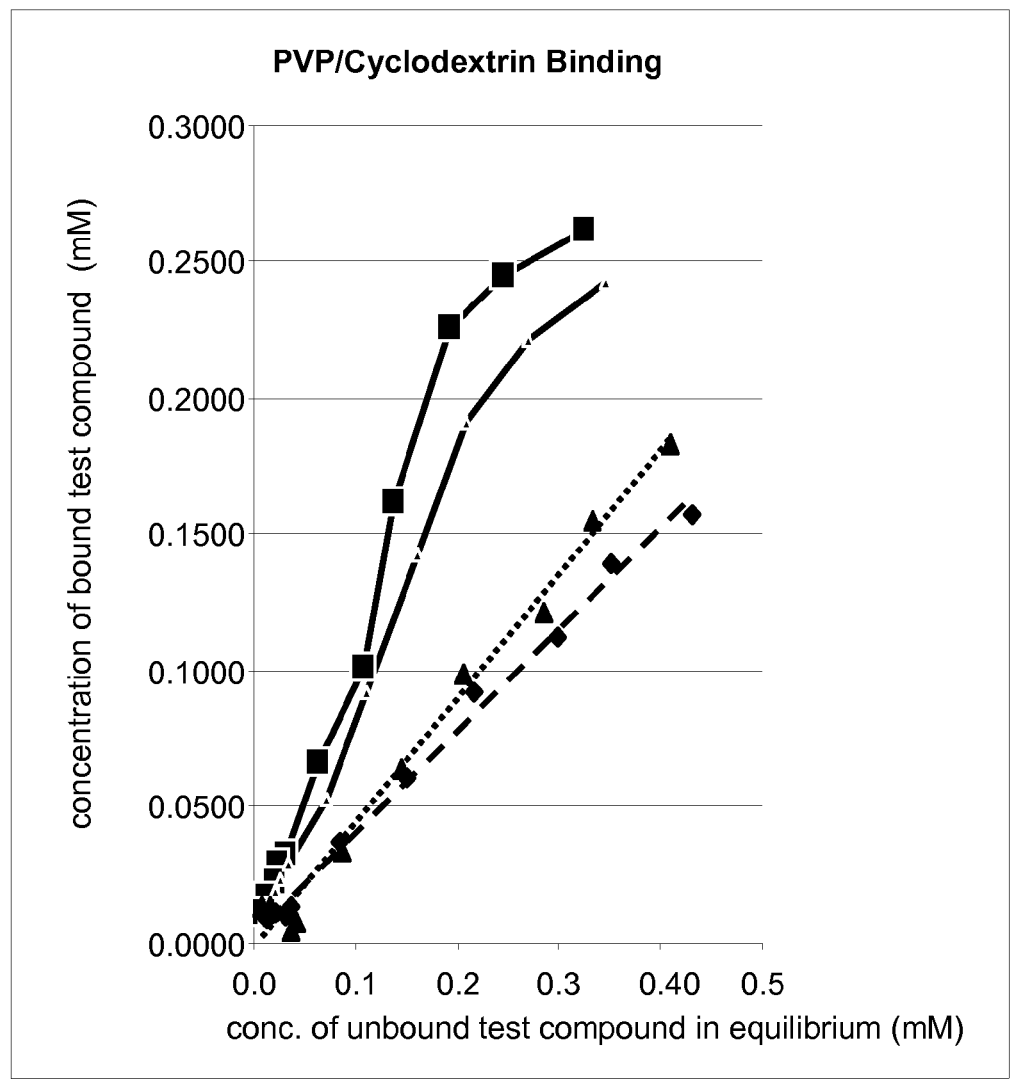

FIG. 5 shows a comparison of the fractional occupation of a test compound (Warfarin, Diclofenac) with the sink compound PVP 25 to the fractional occupation of the test compounds with a combination of sink compounds (beta-hydroxypropyl-cyclodextrine, PVP25). X-axis: concentration of unbound test compound in equilibrium in mM, y-axis: concentration of test compound bound. ━■━ Warfarin with PVP25; ━·━ Diclofenac with PVP25; ♦ Warfarin with PVP 25 and β-hydroxypropyl cyclodextrin (‑ ‑ Linear); ▲ Diclofenac with PVP25 and β-hydroxypropyl cyclodextrin; ( ······· Linear).

Figure 6:
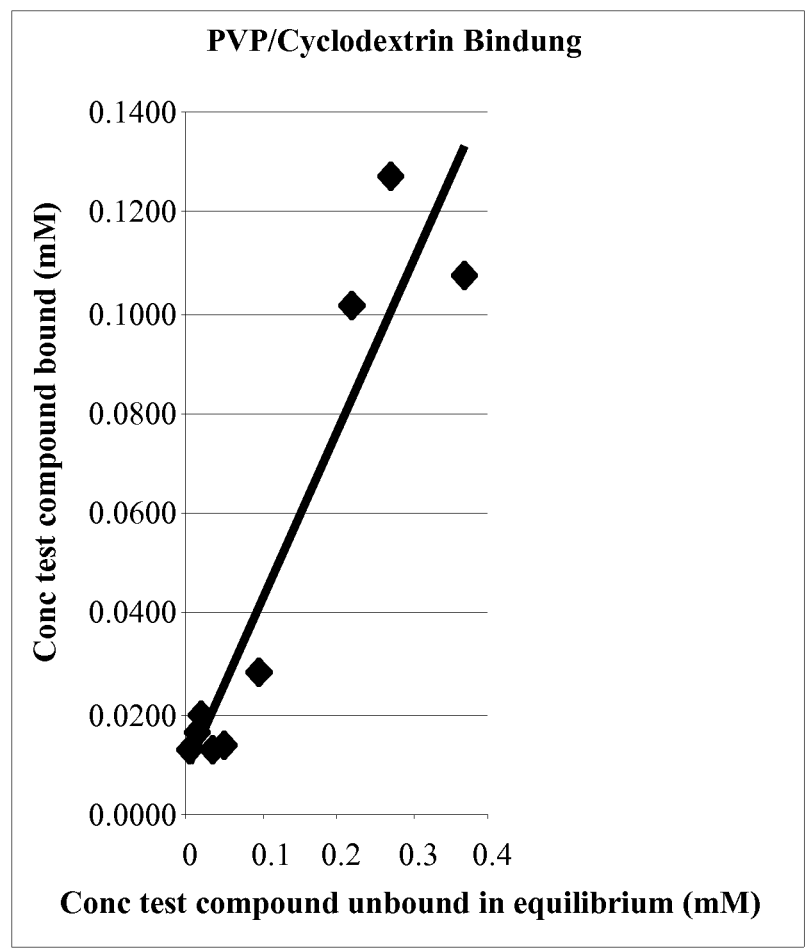
Figure 7:
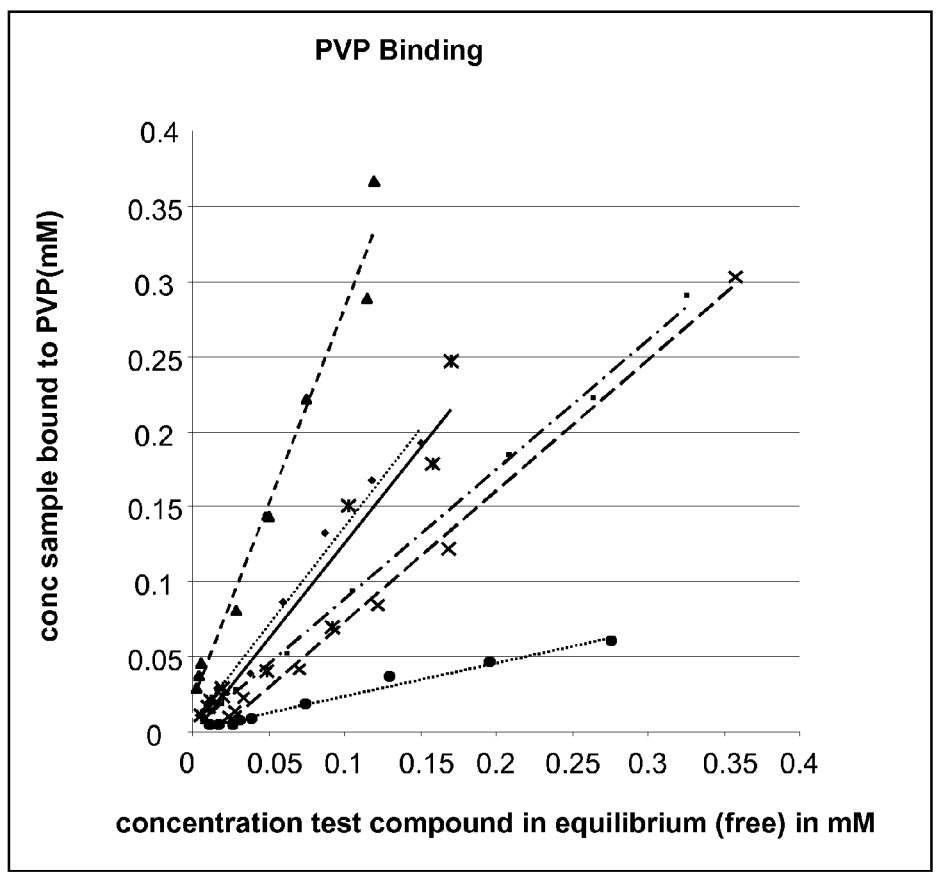

FIG. 6 shows a graphical representation of the fractional occupation of a cardevilol with a combination of sink compounds (beta-hydroxypropyl-cyclodextrine, PVP25). X-axis: concentration of unbound cardevilol in equilibrium in mM, y-axis: concentration of test compound bound. ♦ Carvedilol PVP 25 with β-hydroxypropyl Cyclodextrin FIG. 7 shows a graphical representation of the fractional occupation of a test compounds (Diclofenac, Warfarin, Carvedilol, Naproxen, Proxicam and Glibenclamid) with the sink compound PVP 25. x-axis: total concentration of cardevilol in mM, y-axis: fractional occupation of the cardevilol in % (amount of test compound bound to sink compound). • Diclofenac with PVP25 (·········· Linear); • Warfarin with PVP (— · — Linear); ▲ Carvedilol with PVP 25 (— — — Linear), x Naproxen with PVP25 (— — Linear); ∗ Piroxicam with PVP25 (——— Linear); • Glibenclamid with PVP25 (·········· Linear).

Figure 8:
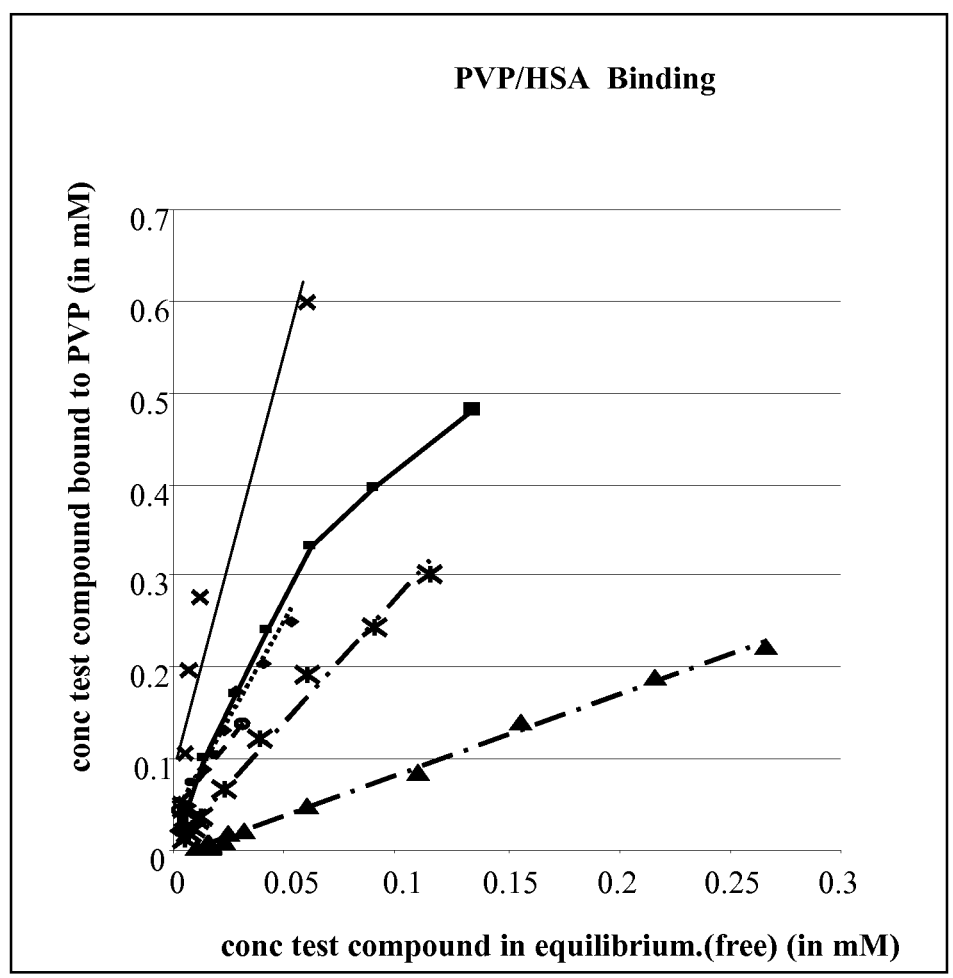
Figure 9A:
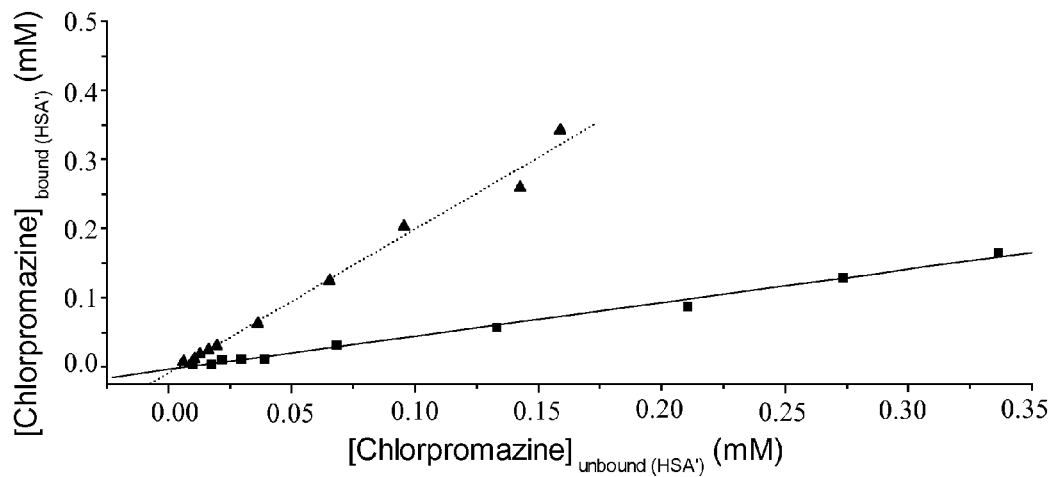
Figure 9B:
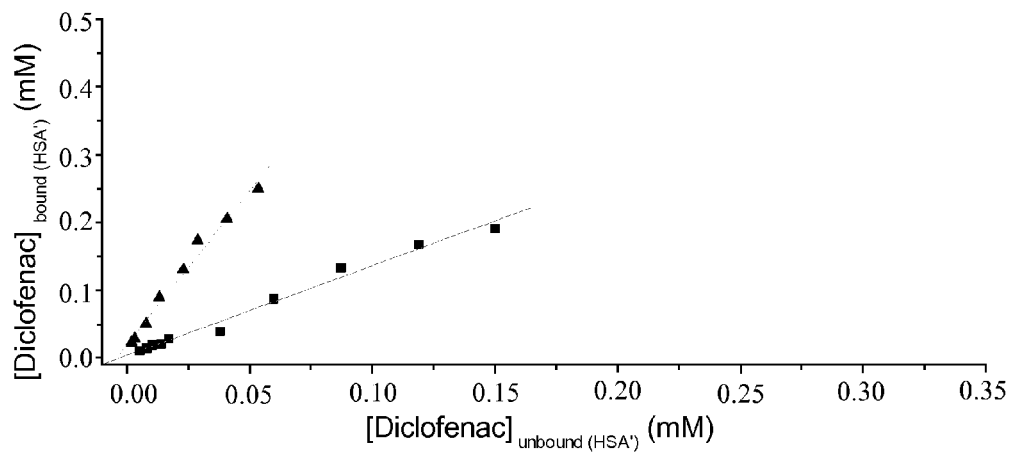
Figure 9C:
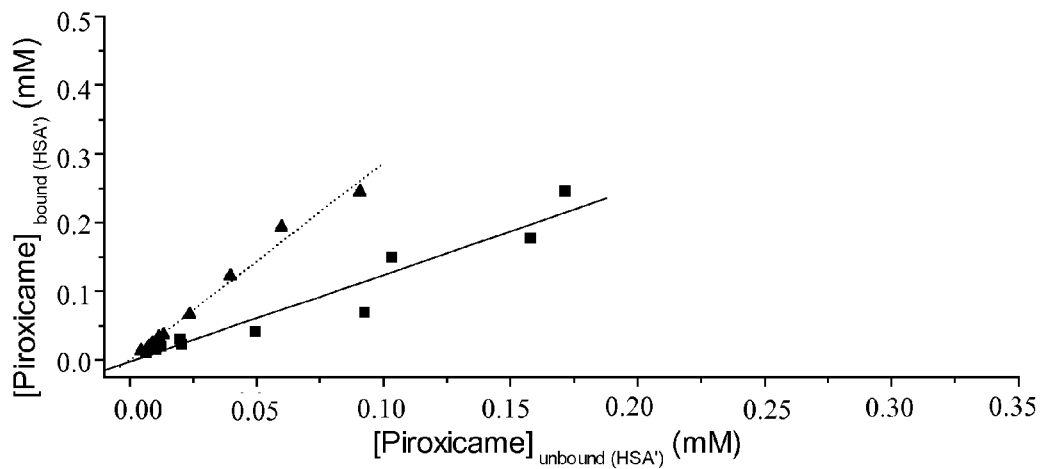
Figure 9D:
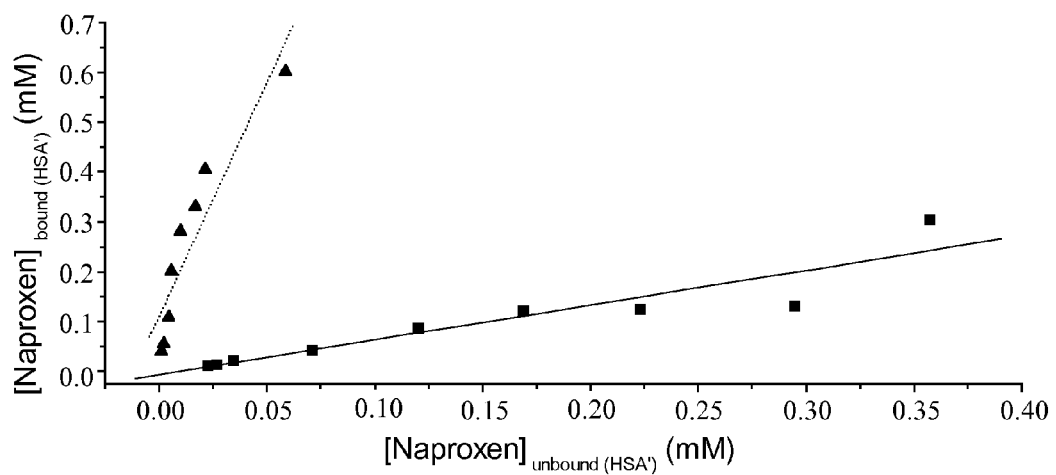
Figure 9E:
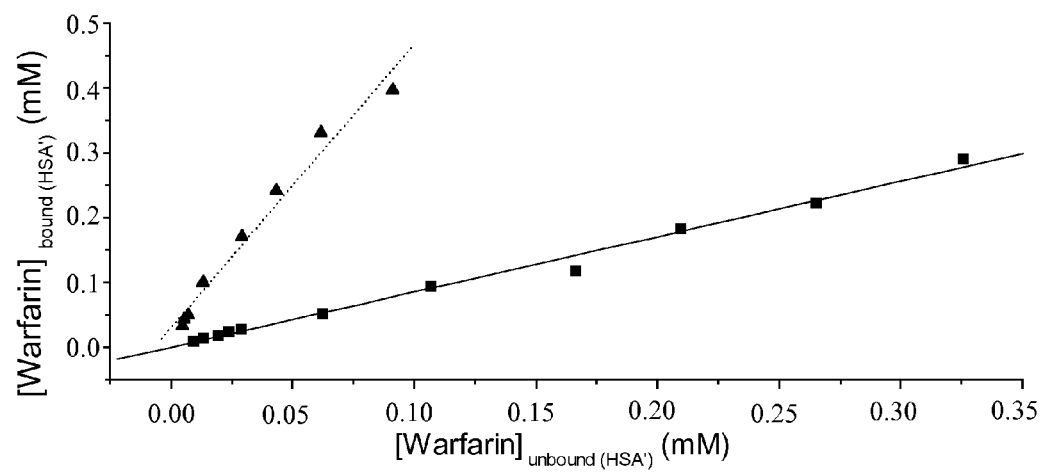
Figure 9F:
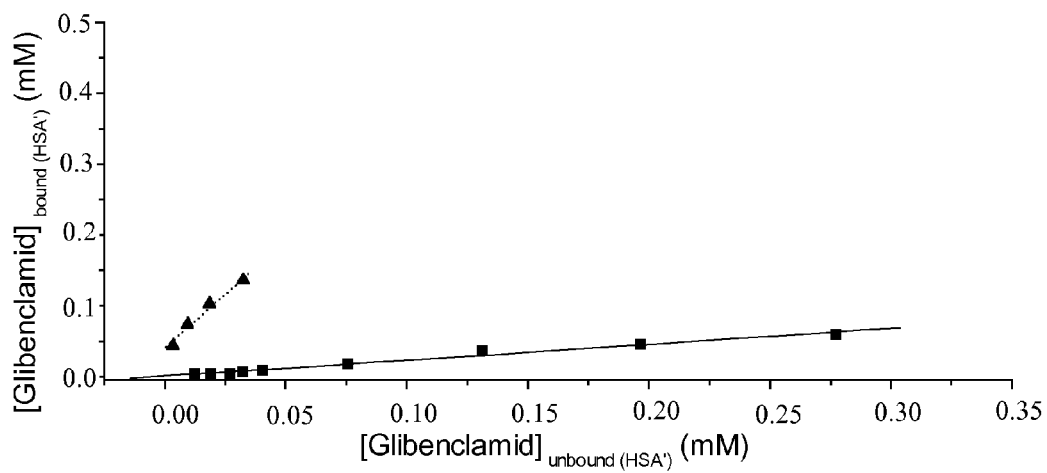

FIG. 8 shows a graphical representation of the fractional occupation of a test compounds (Diclofenac, Warfarin, Carvedilol, Naproxen, Proxicam and Glibenclamid) with the sink compound PVP 25 in the presence of human serum albumin (HSA). x-axis: total concentration of cardevilol in mM, y-axis: fractional occupation of the cardevilol in % (amount of test compound bound to sink compound). • Diclofenac with PVP25 (·········· Linear); —■— Warfarin with PVP (Linear); ▲ Carvedilol with PVP 25 (— · — Linear), x Naproxen with PVP25 (——— Linear); ∗ Piroxicam with PVP25 (—···— Linear); • Glibenclamid with PVP25 (— — — Linear).

FIG. 9 shows a graphical representation of the partition of Chlorpromazine (A), Diclofenac (B), Piroxicame (C), Naproxen (D), Warfarin (E) and Glibenclamid (F) to HSA in the presence of PVP25 (■) and to PVP25 (▲).

Figure 10:
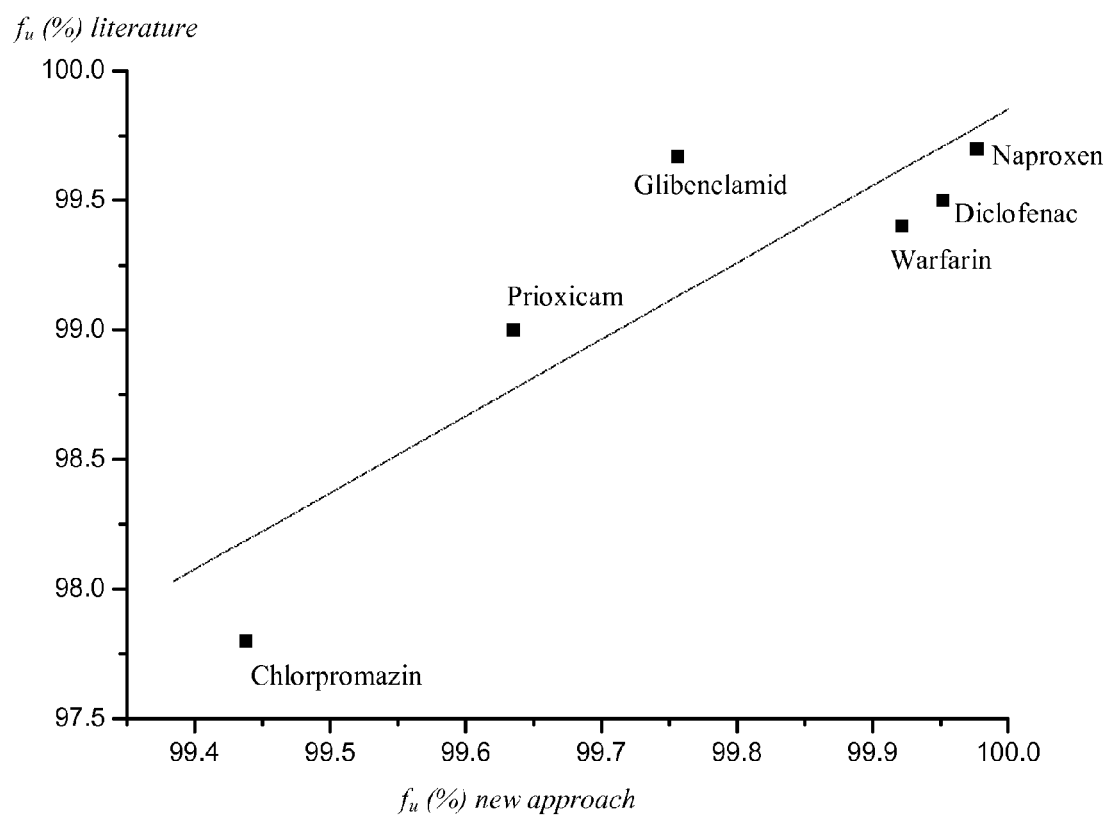

FIG. 10 shows a graphical representation of the determined binding constant with the method of the present invention compared with the literature values.

EXAMPLES

Commercially available reagents referred to in the examples were used according to manufacturer's instructions unless otherwise indicated.

Example 1

Material and Methods 1.1 Dialysis Chambers

A reusable 96-well Micro-Equilibrium dialysis Device 96 chamber was used for the following experiments. The chamber system consists of 10 Teflon™ bars, wherein semipermeable membranes (see 1.2 Membranes) were placed between two Teflon™ bars each to form two compartment of each well.

The assembled Teflon™ block was inserted into a steel frame. To ensure the sealing between the individual wells, the bars are pressed together with steel plate. Said steel plate imposed counter pressure with 8 disc springs upon the Teflon™ bars.

Before each experiment, the Teflon™ bars were cleaned by rinsing four times in ethanol.

1.2 Membranes
MWCO

Following MWCOs were tested in dependency of the additive:

| Additive | [kDa] |
|---|---|
| Micellar agent | 6-8; 12-14 |
| Cyclodextrin | 1 |
| PVP | 3.5 |
| PVP - Cyclodextrin - mixture | 1 |

Membrane Material

A) HTD 96 Dialysis Membrane Strips (regenerated cellulose) with MWCO of 6-8 kDa (HTDialysis, LLC, Catalog Nr 1103) and MWCO of 12-14 kDa (HTDialysis, LLC, Catalog Nr 1101).

The above mentioned membranes were hydrated with deionized water for 60 minutes.

Subsequently, they were treated for 20 minutes with 20% ethanol and then rinsed twice with deionized water.

B) Spektra/Por 6 (regenerated cellulose) with MWCO of 1 kDa (Spectrum Laboratories, Catalog No.: 132640, 45 mmflat width/10 m length) and with MWCO of 3.5 kDa (Spectrum Laboratories, Catalog No.: 132592, 45 mmflat width/10 m length Removal of Heavy Metals:

Heavy Metal cleaning solution comprising EDTA (Spektrum, Cat.: 132908); 1 part wash solution+9 parts H2O distilled.

The 1 h washing, then 5 min in H2O distilled.
Removal of Sulfides 0.1%:
Sulfur cleaning solution A (=Na-sulfite) and
B (=0.4% sulfuric acid) (Spektrum, Cat.: 132 906).
At 80° C. the membranes were washed with a solution comprising 2 parts H2O dist+1 part Solution A. Then the membranes were washed in 60° C. hot H2O for 2 min). The membranes were then washed in a solution comprising 100 parts water and 4 parts Solution B and then they were washed in distilled water for some minutes.

Alternatively, pre-washed membranes were used.

C) Spektra/Por 7 (Regenerated Cellulose) MWCO 3.5 kDa (Spectrum Laboratories, Catalog No.: 132111, 45 mm flat width/5 m length The membrane was washed in distilled water.

1.3 Sink Compounds

Figure 1A:
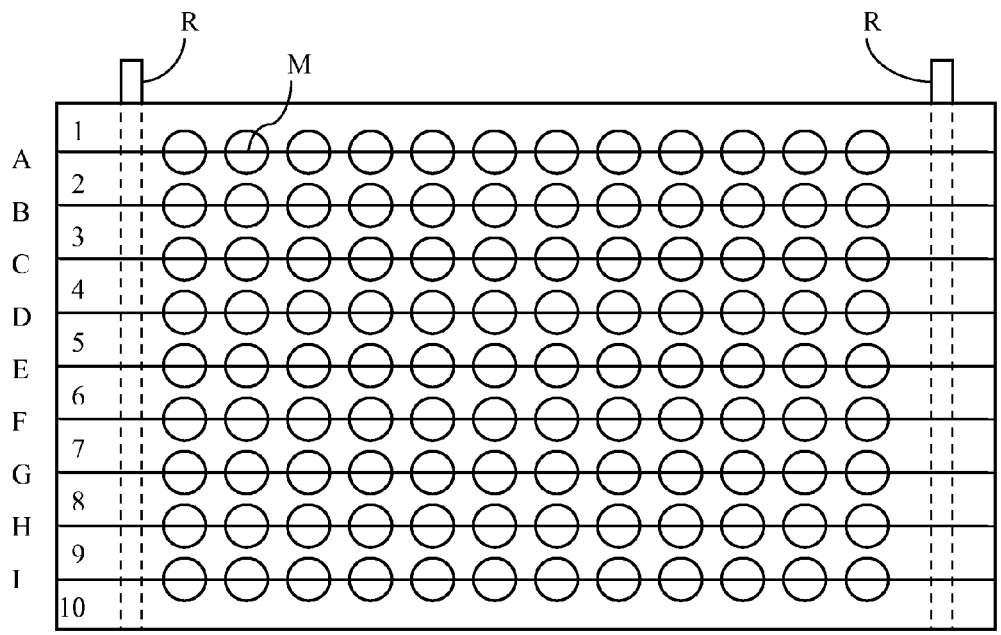
Figure 1B:
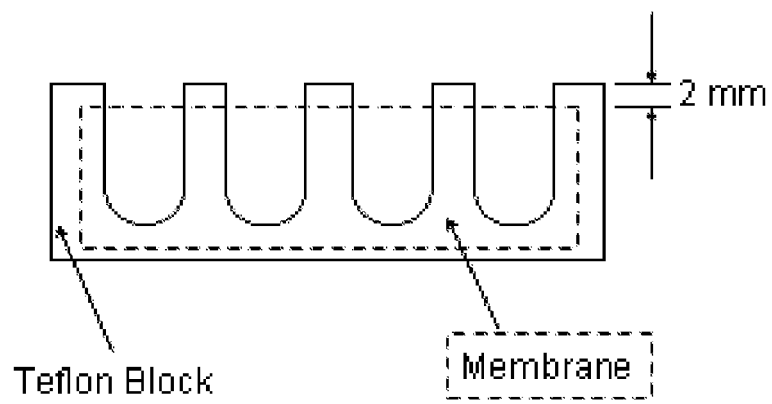
Figure 2:
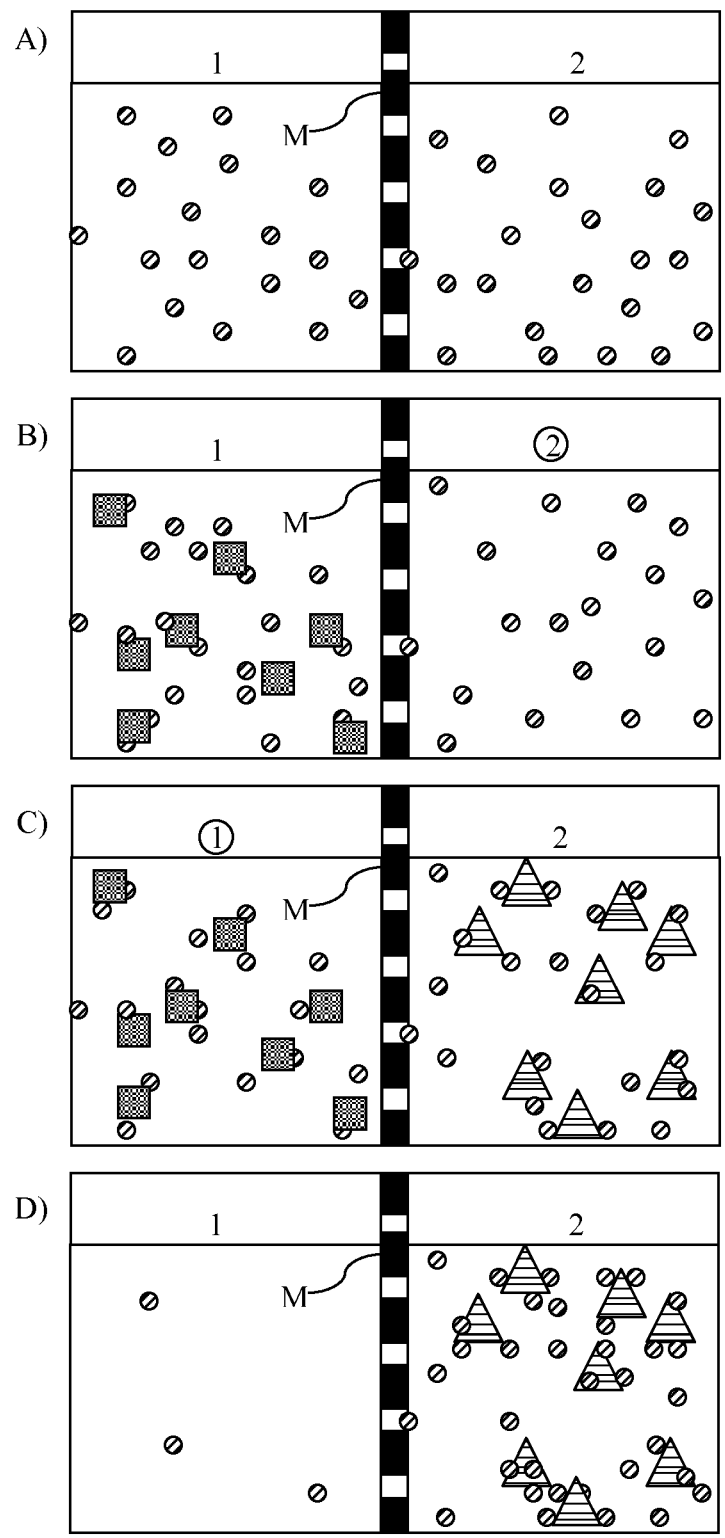
Figure 3:
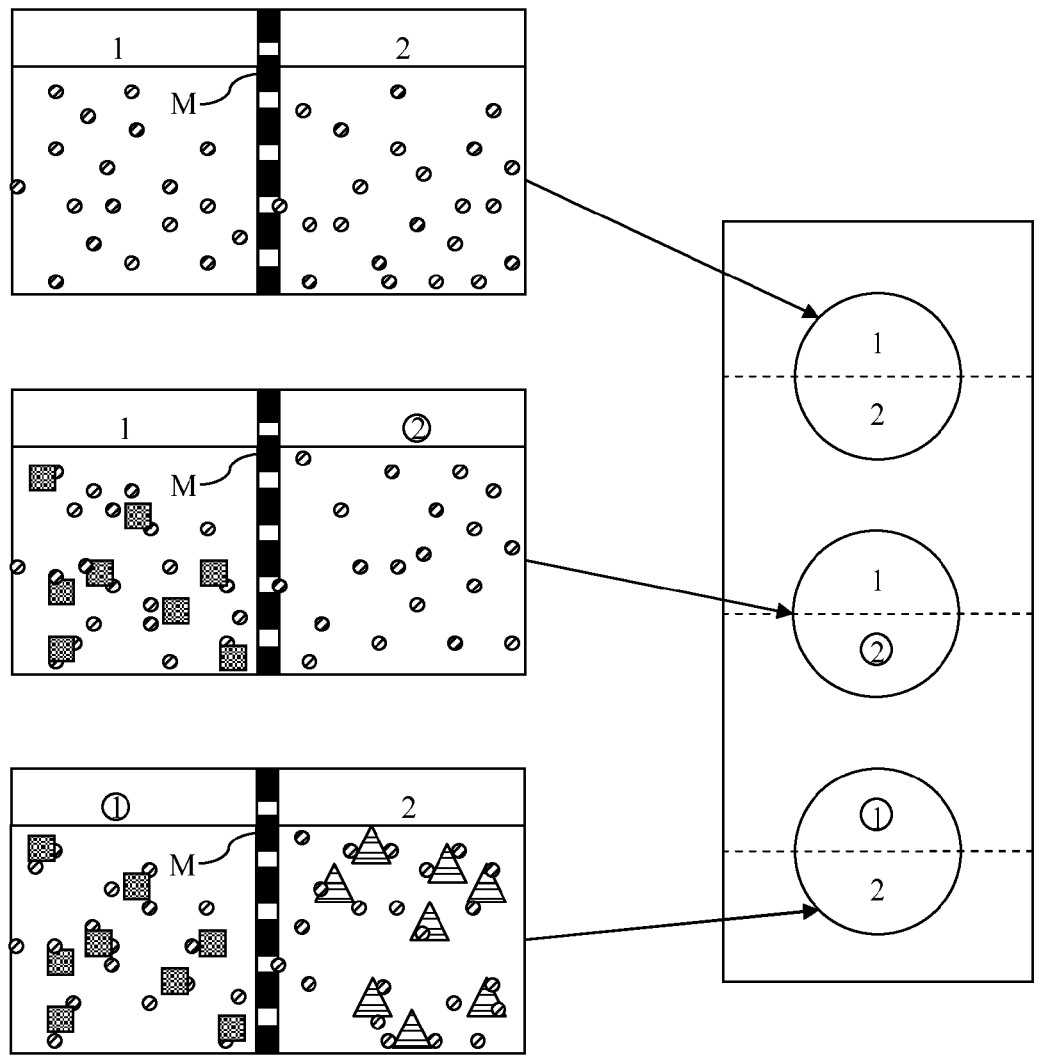
FIG. 3 shows a schematic representation of the method of the present application performed in parallel in 3 two-chamber systems.

A) Cyclodextrine (FIG. 3)

The condition for the use of cyclodextrine is that the molecular weight is bigger than the MWCO of the used membrane to ensure that the sink compound is separated from the sink chamber.

The following cyclodextrins were used:
beta-Hydroxypropxyl-Cyclodextrin
gamma-Cyclodextrin.

Figure 4A:
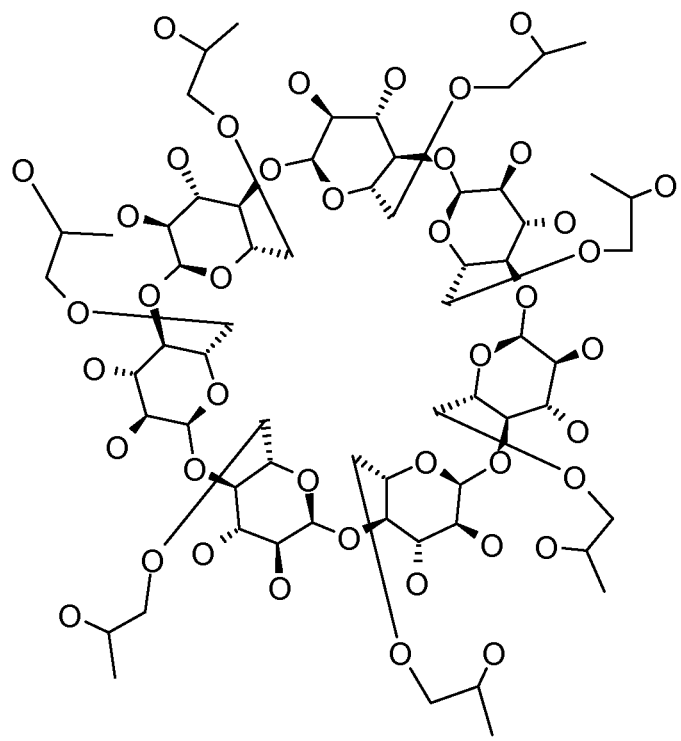
FIG. 4 shows the chemical structure of beta-hydroxypropyl-cyclodextrin (A) and of a polyvinylpyrrolidon monomer (B).
Figure 4B:
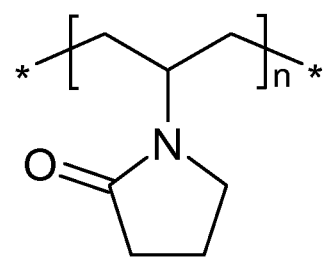

B) Polyvinylpyrrolidon PVP (FIG. 4)

PVP (Polyvidon, Povidon, Povidonum), Homopolymer of N-Vinylpyrrolidon

The molecular weight is usually expressed as the K value. The molecular weight is dependent of the polymerization grade (approx. 2500-3,000,000 Dalton).

Experiments were done with PVP 25 (PVP K-25) with a molecular weight of Mr ~24.000, and PVP 15 (PVP K-15) with a molecular weight of Mr ~10.000.

1.4 Test Compounds
Warfarin ((RS)-4-hydroxy-3-(3-oxo-1-phenylbutyl)-2H-chromen-2-one),
Furosemide (4-chloro-2-(furan-2-ylmethylamino)-5-sulfamoylbenzoic acid)

Diclofenac (2-(2-(2,6-dichlorophenylamino)phenyl)acetic acid)
Verapamil (2-(3,4-dimethoxyphenyl)-5-[2-(3,4-dimethoxyphenyl)ethyl-methyl-amino]-2-(1-methylethyl)pentanenitrile)
Chlorpromazine (3-(2-chloro-10H-phenothiazin-10-yl)-N,N-dimethyl-propan-1-amine)
Carvedilol (3-(9H-carbazol-4-yloxy)-2-hydroxypropyl] [2-(2-methoxyphenoxy)ethyl]amine)
Naproxen ((+)-(S)-2-(6-methoxynaphthalen-2-yl)propanoic acid)
Piroxicam ((8E)-8-[hydroxy-(pyridin-2-ylamino)methylidene]-9-methyl-10,10-dioxo-10λ6-thia-9-azabicyclo[4.4.0]deca-1,3,5-trien-7-one)
Glibenclamide (5-chloro-N-(4-[N-(cyclohexylcarbamoyl)sulfamoyl]phenethyl)-2-methoxybenzamide)

1.5: Experimental Procedure
1) preparing the membranes (see example 2) and assembling the dialysis chamber in example 1.
2) The protein chamber (chamber 2) is filled with buffer and the other excipients to the final volume of approximately 100-150 ul. It is important that on each side the volume is exactly the same.
Volume per chamber:
with pure cyclodextrines as sink compound the volume in each chamber was 147 μl (γ-Cyclodextrin 2.5% (m/V))
with PVP and PVP in combination with cyclodextrines as sink compound in chamber the volume was 100 μl. (PVP 15 4% (m/V), PVP 25 4% (m/V), PVP 25 4% (m/V)+β-Hydroxypropyl-cyclodextrin 4% (m/V))
Buffer: 50 mM TAPSO, pH 7.4, isotonised with NaCl to the total concentration of 154 mM, addition excipient different depending on excipient
End Concentration of the test compound: 0.02 mM till 0.6 mM
End concentration of HSA: 60 mM
End concentration of DMSO: 6% (V/V)
The DMSO stock solution is added at the end because it takes long but the chambers has to be filled rather fast due to the risk that the membrane dries out.
3) All pipetting steps were automated (Tecan)
4) To prevent evaporation the Teflon™ assembly was covered with an adhesive film (Cat. Nr.: 1102; HT-Dialysis).
5) The chamber system was shaken for 1 hour, then incubated over night (approximately 12 hours). Long duration shaking should be avoided due to the risk of higher evaporation caused by the generated heat.
6) After reaching the equilibrium, a sample from the sink chamber (reference, binding study II with sink compound and HSA), or from the protein chamber (reference, binding study I with sink compound alone) was transferred to a half-area UV-plate and analyzed spectrometrically (spectra max, 190 Plate Reader; 250-500 nm) or it was analysed by HPLC.

1.6 Analysis of Measured Data
The distribution coefficient and the binding constant can be calculated with binding studies. The binding of drugs to HSA is a reversible process which can be described by the following equilibrium [4]

$$[D_u]+[HSA]\cdot[D\cdot HSA]$$

where square brackets are used to denote concentrations and $[D_u]$, [HSA] and [D·HSA] are the concentrations of non HSA-bound drug, HSA and HSA-bound drug respectively.
The binding constant $K_{HSA}$ can be converted to the fraction unbound $f_u$ with the following formula derived from the law of mass:

$$f_u = \frac{100}{1 + K_{HSA} \cdot [HSA]} \quad (1)$$

The binding constant to HSA ($K_{HSA}$) (2) can be calculated from the combination of partition coefficients to PVP ($DC_{PVP}$) (3) and to HSA in the presence of PVP ($DC_{HSA'}$) (3).

$$K_{HSA}=DC_{PVP}\cdot DC_{HSA'} \quad (2)$$

From Binding Study I:

$$VK_{PVP} = \frac{[D-PVP]}{[D_{u(PVP)}]} = \frac{m_{D_{b(PVP)}}}{m_{D_{u(PVP)}}} \cdot \frac{V_{total}-V_{PVP}}{V_{PVP}} = \frac{m_{D_{ref}}-m_{D_{u(PVP)}}}{m_{D_{u(PVP)}}} \quad (3)$$

From Binding study II:

$$VK_{HSA'} = \frac{[D-HSA']}{[D_{u(HSA')}]} = \frac{m_{D_{b(HSA')}}}{m_{D_{u(HSA')}}} \cdot \frac{V_{total}-V_{HSA}}{V_{HSA}} = \frac{m_{D_{ref}}-m_{D_{u(HSA')}}}{m_{D_{u(HSA')}}} \quad (4)$$

Where [D–HSA'] and [D–PVP] are the HSA-bound drug in the presence of PVP and the PVP-bound drug respectively. $V_{total}$ is total volume in the dialysis chamber (200 μl) and $V_{HSA}$ and $V_{PVP}$ are the volumes of HSA and PVP 25, which can be calculated from the density and the weighted sample $$V_{HSA} = \frac{m_{HSA}}{\rho_{HSA}}$$

$\rho_{HSA}=1.4$ g/cm$^3$ and $\rho_{PVP}=1.2$ g/cm$^3$. For determining the density PVP had to be melted and there are variations due to inclusion of air. Therefore, real density are based on information from BASF (manufacturer).
The above mentioned equation can be applied analogous for determining the concentration of the unbound/bound test compound in equilibrium with another sink compound.

Example 2

Comparison of Beta-Hydroxypropyl-Cyclodextrine with Gamma-Cyclodextrine

| | |
|---|---|
| Membrane | cut off 1 kDa, Spektra/Por 6 |
| Concentration Warfarin | 0.01 mM to 0.4 mM |
| Concentration of beta-hydroxypropyl-cyclodextrine | 1%; 5%; 10% (m/V) |
| Concentration of gamma Cyclodextrin | 2.5% (m/V) |
| Analysis | UV |

The results are shown in table 1. With a 10% solution of beta-hydroxypropyl Cyclodextrin more than 30% of the test compound can be bound. The affinity to gamma-Cyclodextrin is considerable lower than with beta-hydroxypropyl-cyclodextrine (2.5 times higher concentration of gamma-Cyclodextrin is needed to achieve the same fractional occupation).

TABLE 1

Exipient binding levels measured for Warfarin

| Excipient | $f_b$(%) | SD |
|---|---|---|
| γ-Cyclodextrin 2.5% (m/V) | 6.0 | 2.5 |
| β-Hydroxypropyl-cyclodextrin 1% (m/V) | 6.8 | 2.1 |
| β-Hydroxypropyl-cyclodextrin 10% (m/V) | 27.6 | 4.4 |

Example 3

Assay with Beta-Hydroxypropyl-Cyclodextrine as Sink Compound

The test conditions are as described above unless specifically mentioned.

| | |
|---|---|
| Membrane: | cut off: 1 kDa; Spektra/por 6 |
| Concentration test compound: | 0.02 mM-0.06 mM |
| Concentration of beta-hydroxypropyl-cyclodextrine: | 10% (m/V) |
| Duration of incubation: | Over night (approx. 12 h) |
| Tecan | |
| Total volume per well or chamber: | 294 µl total volume (each chamber: 147 µl, see above) |
| DMSO - concentration: | 6% (V/V) |
| Analysis: | Spektra max, 50 ul |

TABLE 2

Average Binding of test compounds to beta-hydroxypropyl-cyclodextrine

| Test substance | Carba-mazepin | Warfarin | Diclo-fenac | Quinine | Ceftri-axone |
|---|---|---|---|---|---|
| Molecular Weight | 236.27 | 308.33 | 296.15 | 324.4 | 554.6 |
| Average Binding [%] | 31.3 | 26.9 | 23.1 | 21.6 | 14.2 |

Conclusion: the lower the molecular weight of the test compound, the better the affinity to beta-hydroxypropyl-cyclodextrine

Example 4

Comparison of PVP 15 with PVP 25

Test conditions are described as above unless specifically mentioned.
Concentrations of the drugs: 0.02-0.6 mM
Amounts of PVP 15 and PVP25: each 40 g/l

TABLE 3

Average Binding of test compounds to PVP15 and PVP25.

| Test Substance | Warfarin | Furosemid | Diclo-fenac | Verap-amil | Chlor-promazin |
|---|---|---|---|---|---|
| Average binding [%] to PVP15 | 34.5 | 37.0 | 21.7 | n.d. | 17.0 |
| Average binding [%] to PVP25 | 51.4 | 49.4 | 46.4 | 13.1 | n.d. |

(n.d. = not determined)

The test substances have a higher affinity to PVP 25 than to PVP 15. Therefore, the experiments of following examples were done with PVP 25.

Example 5

Assay with Combination of PVP25 and Cyclodextrin as Sink Compound

| | |
|---|---|
| Membrane | cut off 1 kDa; Spektra/Por |
| concentration of PVP 25 | 4.0% (m/V) |
| concentration beta-hydroxypropylcyclodextrin | 4.0% (m/V) |
| Concentration of the test compounds (warfarin, diclofenac) | 0.02 mM to 0.6 mM |
| Tecan for pipeting: | |
| Total volume per well | 100 µl per well |
| DMSO - concentration | 6% (V/V) |
| Analysis | Spektra max, 50 ul |

The results are shown in FIGS. 5 and 6. The use of beta-hydroxypropyl cyclodextrin and PVP25 moves the equilibrium less towards complex of drug and sink compound than the use of PVP 25 alone (see FIG. 6).

TABLE 4

Summary of exipient binding levels measured for Warfarin (including results from Examples 2 and 4.

| Excipient | $f_b$(%) | SD |
|---|---|---|
| γ-Cyclodextrin 2.5% (m/V) | 6.0 | 2.5 |
| β-Hydroxypropyl-cyclodextrin 1% (m/V) | 6.8 | 2.1 |
| β-Hydroxypropyl-cyclodextrin 10% (m/V) | 27.6 | 4.4 |
| PVP 15 4% (m/V) | 34.5 | 2.9 |
| PVP 25 4% (m/V) | 51.4 | 3.1 |
| PVP 25 4% (m/V) + β-Hydroxypropyl-cyclodextrin 4% (m/V) | 27.9 | 1.8 |

Example 6

Assay with PVP 25 and Human Serum Albumin (HSA)

The same test conditions were used as described in Example 5 except for the test compound Carvedilol was used. The results are shown in FIG. 8 and FIG. 9.

| | |
|---|---|
| membrane | Spektra/Por 6, MWCO 3.5 kDa, |
| concentration PVP (sink compound) | 4.0% (m/V) |
| concentration HSA (unspecific protein) | 60 mM |
| Concentration of test compound | 0.02 mM to 0.6 mM |
| DMSO - concentration | 6% |
| volume per compartment | 100 µl |
| Control | PVP alone |
| Tecan | |
| duration of dialysis | over night (approx. 12 h) |
| analysis | HPLC/Program: ATHESA |
| injection volume: | 4 µl |

HPLC Conditions:

Analytics was carried out on an HPLC-system (Agilent 1100). The separations were performed on a RP column (Chromolith flash, RP18e, 4.6×25 mm). Samples were eluted with gradient of water with 0.05% formic acid (A) and Acetonitril (B). Gradient conditions: initial 5% B, 0.4 min 95% B; 1 min 95% B; 1.1 min 5% B.

Results with test compound and PVP are shown in FIG. 7 and results with test compounds, PVP25 and HSA are shown in FIGS. 8 and 9.

Example 7

Comparison with Literature Values

The determined binding levels of the test compound in example 6 ("new approach") were compared with the values determined with conventional methods (literature values). The results are shown in table 2 and FIG. 10.

TABLE 5 binding levels of test compounds from literature and derived from example 6.

| Compound | $f_u(\%)^{newApproach}$ | $f_u(\%)^{Literature}$ | Lit ref. |
|---|---|---|---|
| Chlorpromazine | 99.44 | 97.80 | Kratochwil, N. A., et al., *Predicting plasma protein binding of drugs: a new approach*. Biochem Pharmacol, 2002. 64(9): p. 1355-74 |
| Piroxicame | 99.64 | 99.0 | Dollery, C., *Therapeutic Drugs*. second ed. Churchill Livingstone. Vol. 2. 1999. |
| Warfarin | 99.92 | 99.4 | [Kratochwil, N. A., et al., *Predicting plasma protein binding of drugs: a new approach*. Biochem Pharmacol, 2002. 64(9): p. 1355-74 |
| Diclofenac | 99.95 | 99.5 | Kratochwil, N. A., et al., *Predicting plasma protein binding of drugs: a new approach*. Biochem Pharmacol, 2002. 64(9): p. 1355-74 |
| Naproxen | 99.98 | 99.7 | Dollery, C., *Therapeutic Drugs*. second ed. Churchill Livingstone. Vol. 2. 1999 |
| Glibenclamid | 99.95 | 99.67 | Inhouse (with conventional methods) |

The invention claimed is:

1. A method for determining the binding constant of a high affinity compound of interest to proteins comprising the following steps:
   a) adding the high affinity compound to a two-chamber system, wherein the two chambers are separated by a semipermeable membrane, which is permeable for the high affinity compound of interest, and
      determining the amount of the high affinity compound of interest in one of the chambers after the distribution equilibrium has been reached,
   b) adding a sink compound wherein the sink compound is polyvinylpyrrolidone(PVP) or cyclodextrin to either one of the chambers whereby the sink compound can not permeate the membrane, and
      determining the distribution coefficient of the high affinity compound of interest to the sink compound after the distribution equilibrium has been reached,
   c) adding a plasma protein to the other chamber used in step b) wherein the high affinity compound of interest and the sink compound have been added, whereby the plasma protein can not permeate the membrane, and
      determining the distribution coefficient of the high affinity compound of interest to the plasma protein in the presence of a sink compound after the distribution equilibrium has been reached, wherein said plasma protein is serum albumin and
   d) determining the binding constant of the high affinity compound of interest with the distribution coefficient of steps b) and c).

2. The method according to claim 1 wherein the filter is a size selective membrane.

3. The method according to claim 1 wherein the sink compound is PVP25.

4. The method according to claim 1 wherein the steps a), b) and c) are performed in parallel.

5. The method according to claim 1, wherein the semipermeable membrane is regenerated cellulose.

6. The method according to claim 5, wherein the regenerated cellulose is HTD 96 Dialysis Membrane Strips; Spektra/Por. 6 or Spektra/Por. 7.

7. The method according to claim 2 wherein the steps a), b) and c) are performed in parallel.

8. The method according to claim 4, wherein the semipermeable membrane is regenerated cellulose.

9. The method according to claim 2 wherein the sink compound is PVP25.

* * * * *